(12) United States Patent
Delurio et al.

(10) Patent No.: US 8,128,700 B2
(45) Date of Patent: Mar. 6, 2012

(54) ALLOGRAFT INTERVERTEBRAL IMPLANT AND METHOD OF MANUFACTURING THE SAME

(75) Inventors: Robert J. Delurio, Aston, PA (US); Ryan Walsh, Douglassville, PA (US); Joshua McManus, Downingtown, PA (US)

(73) Assignee: Synthes USA, LLC, West Chester, PA (US)

( * ) Notice: Subject to any disclaimer, the term of this patent is extended or adjusted under 35 U.S.C. 154(b) by 1181 days.

(21) Appl. No.: 11/854,132

(22) Filed: Sep. 12, 2007

(65) Prior Publication Data

US 2008/0082173 A1    Apr. 3, 2008

Related U.S. Application Data

(60) Provisional application No. 60/844,515, filed on Sep. 13, 2006.

(51) Int. Cl.
*A61F 2/44* (2006.01)

(52) U.S. Cl. ............... 623/17.15; 623/17.11; 623/17.16

(58) Field of Classification Search ..... 623/17.11–17.16
See application file for complete search history.

(56) References Cited

U.S. PATENT DOCUMENTS

RE38,614 E * 10/2004 Paul et al. ................. 623/17.11

(Continued)

*Primary Examiner* — Thomas C. Barrett
*Assistant Examiner* — Andrew Yang
(74) *Attorney, Agent, or Firm* — Stradley Ronon Stevens & Young LLP

(57) ABSTRACT

The present invention is directed to an allograft intervertebral implant sized and configured for insertion between adjacent vertebral bodies in a spinal fusion surgery. The implant is preferably manufactured from two or more pieces of allograft bone joined together by a joint, more preferably a dovetail joint. The dovetail joint being sized and configured to substantially follow the exterior shape or surface (e.g. perimeter) of the intervertebral implant. The intervertebral implant may also include one or more bone pins for joining the allograft pieces, the pins being inserted into the implant at an angle substantially perpendicular with respect to the dovetail joint. The intervertebral implant may also include one or more through-bores for receiving ostegenic or bone graft material. The intervertebral implant is preferably sized and configured for insertion during a T-PLIF or PLIF procedure.

33 Claims, 11 Drawing Sheets

U.S. PATENT DOCUMENTS 7,018,412 B2 * 3/2006 Ferreira et al. ............. 623/17.11
2004/0078078 A1 * 4/2004 Shepard .................... 623/17.11
2005/0125062 A1 * 6/2005 Biedermann et al. ...... 623/17.11

* cited by examiner

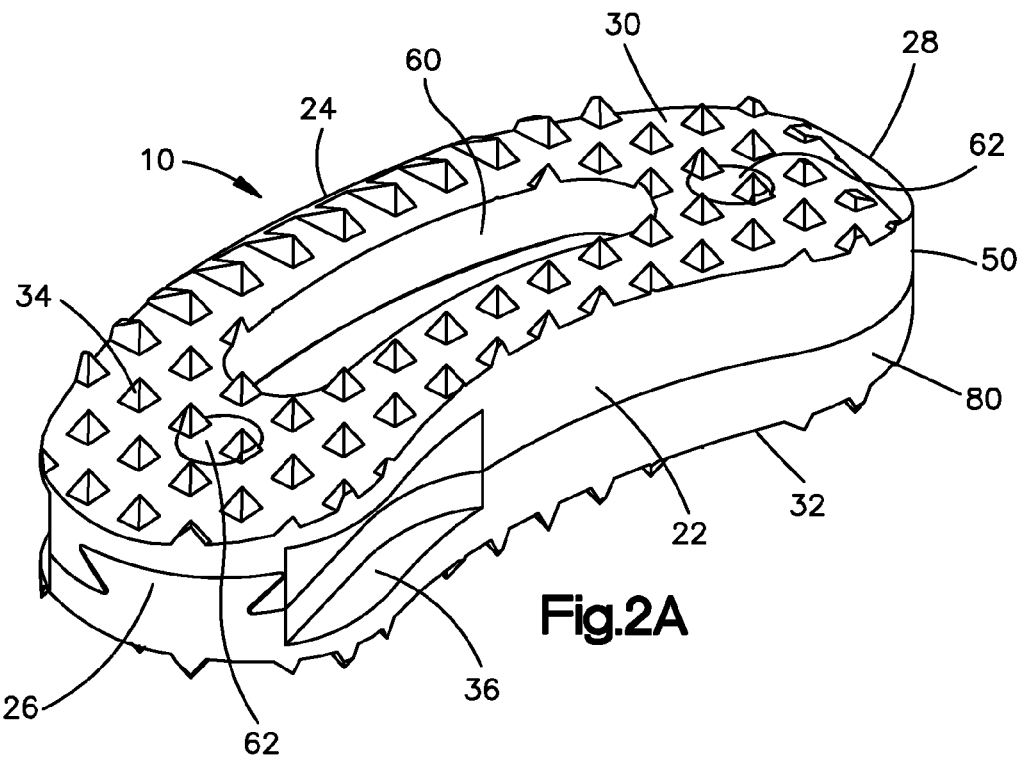
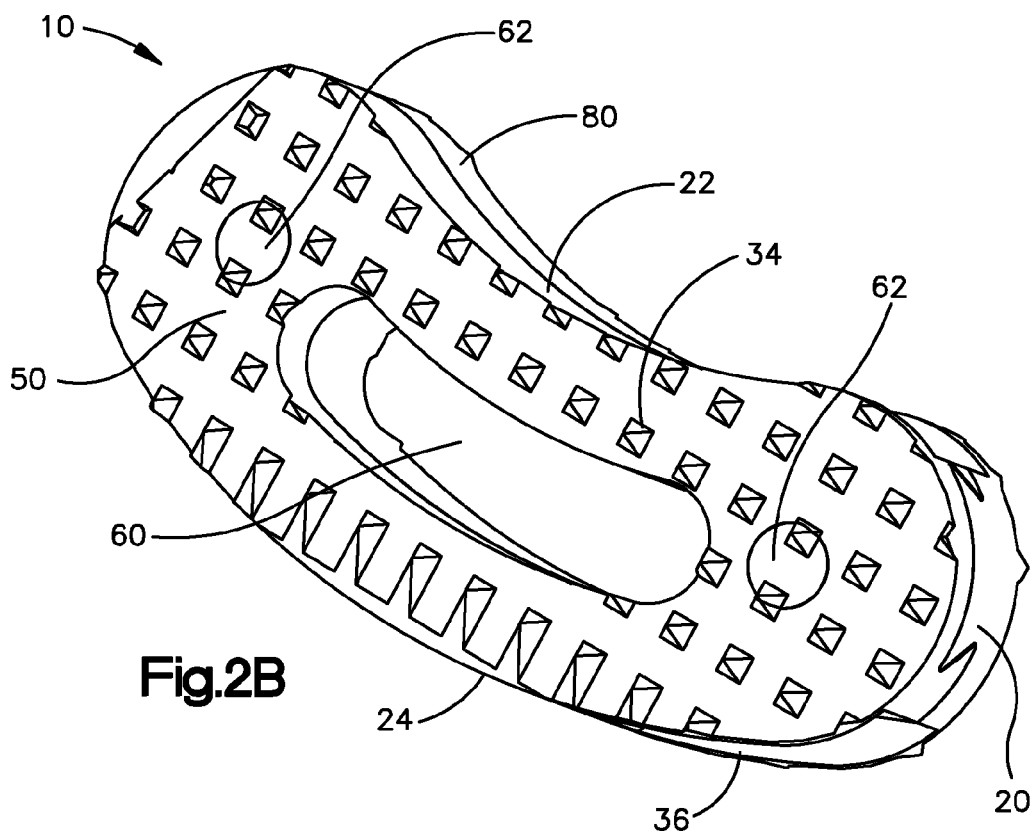

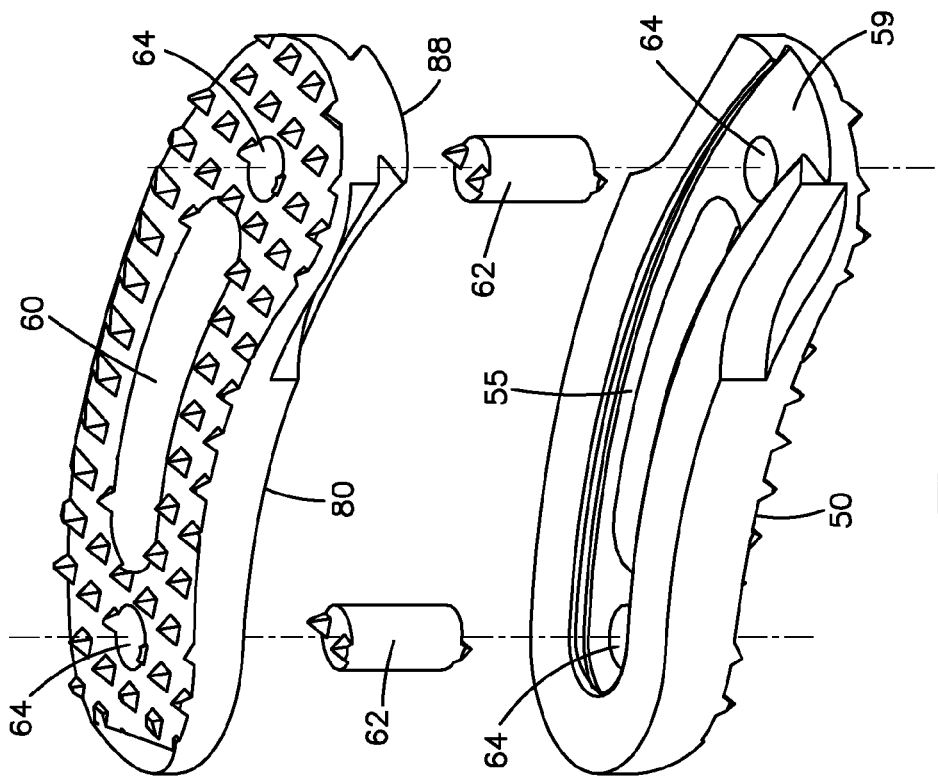
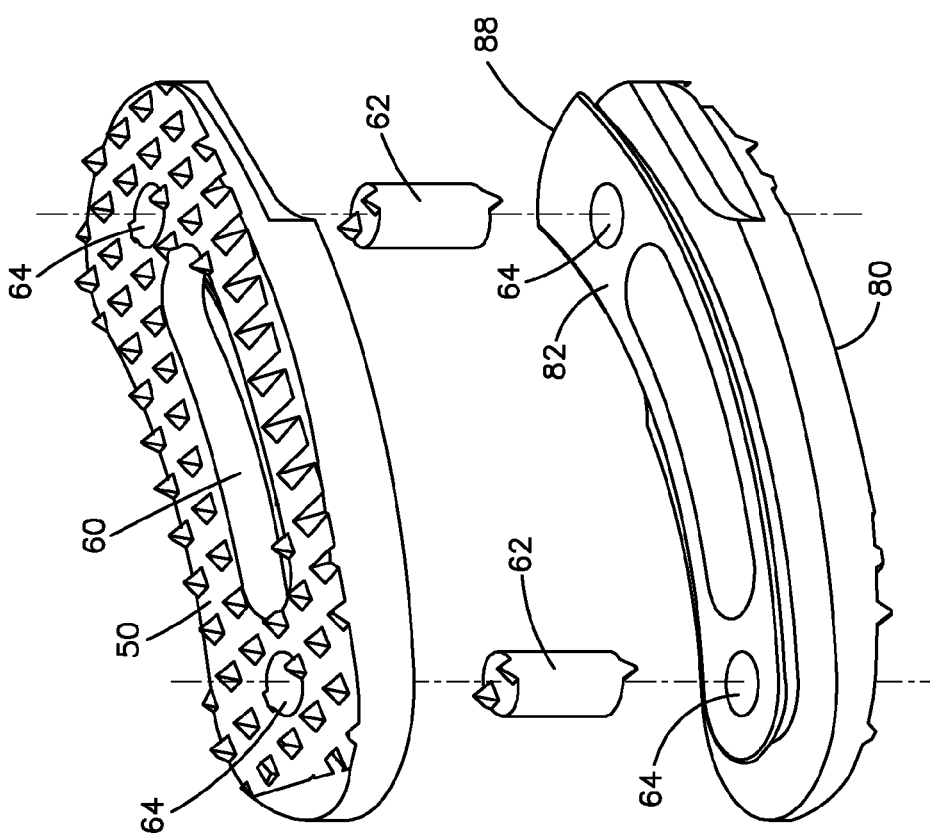
Fig.2D
Fig.2C

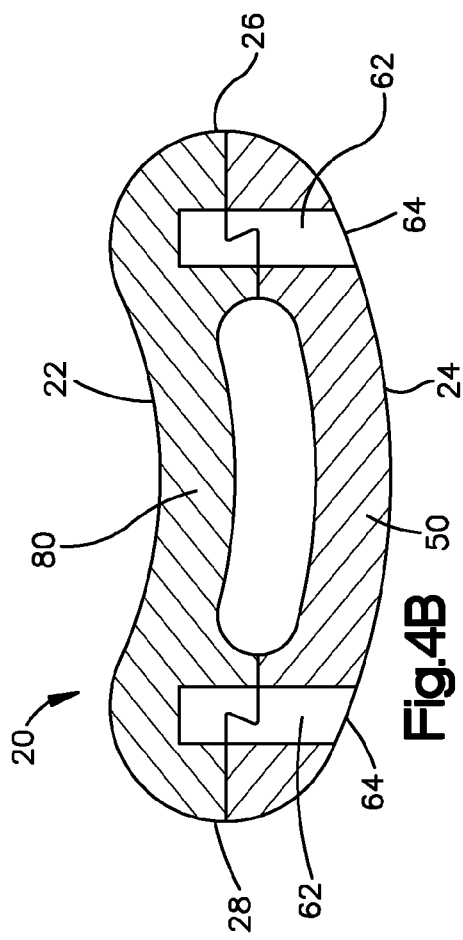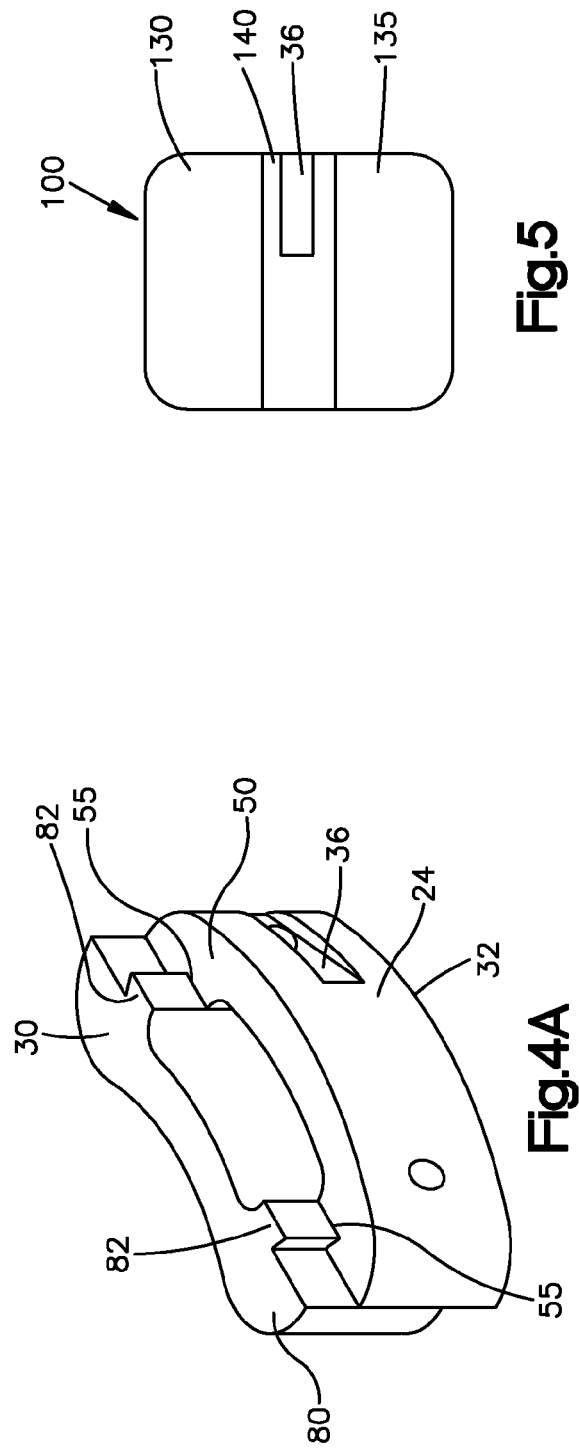

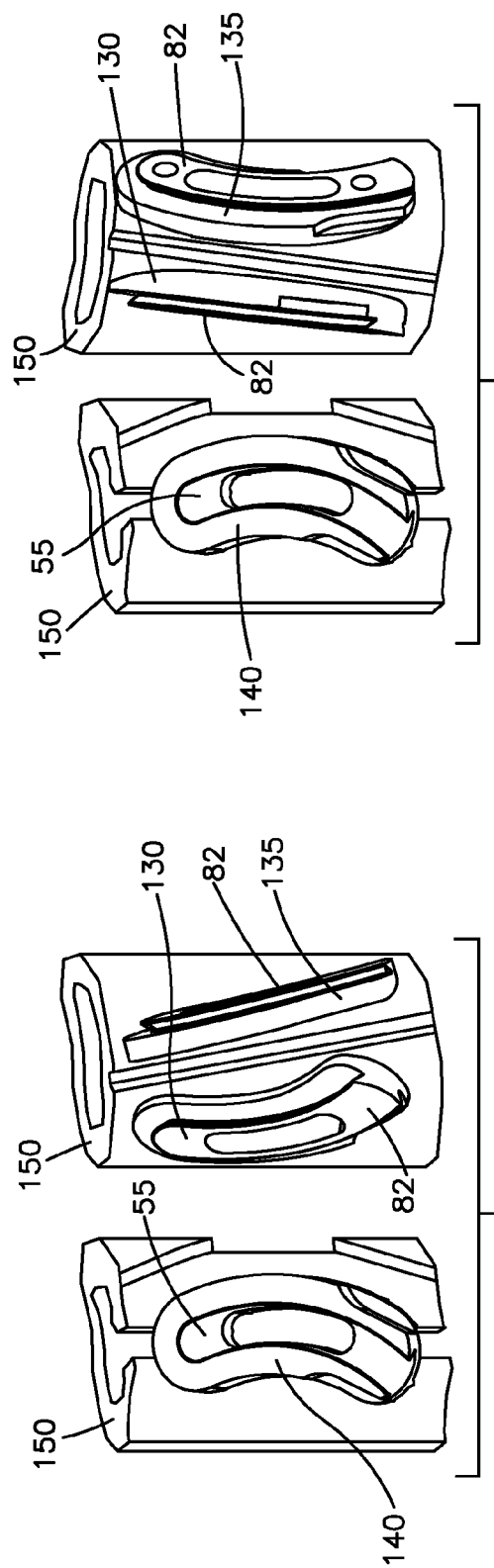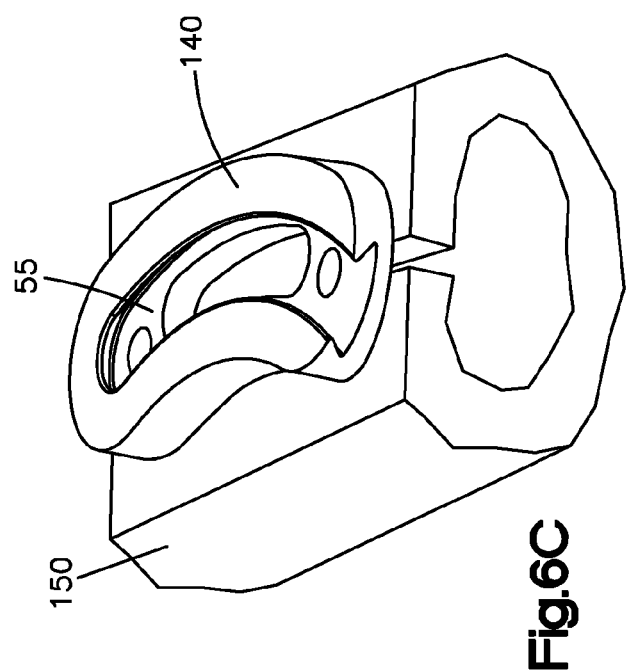

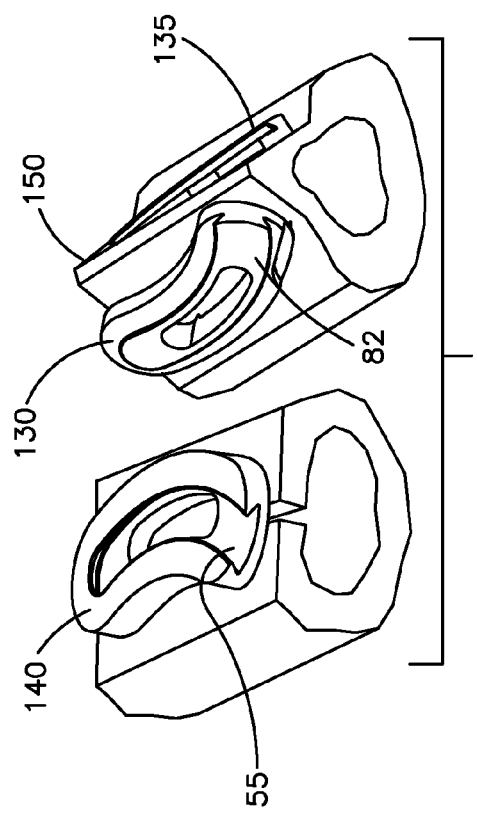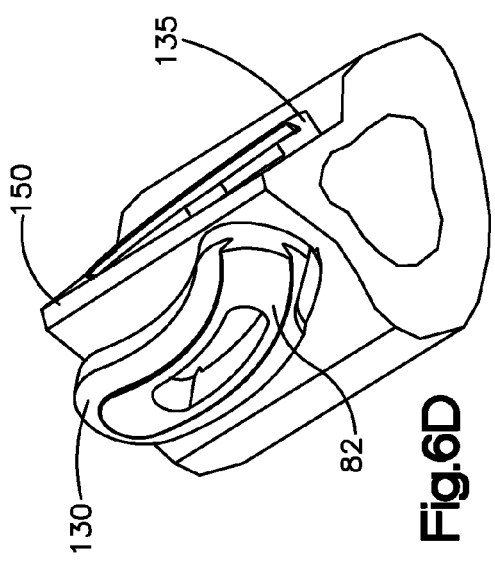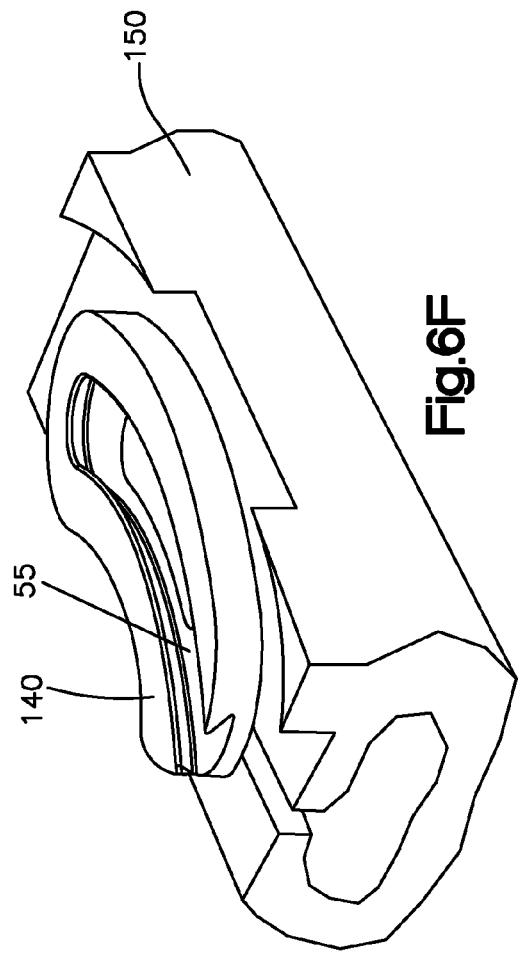

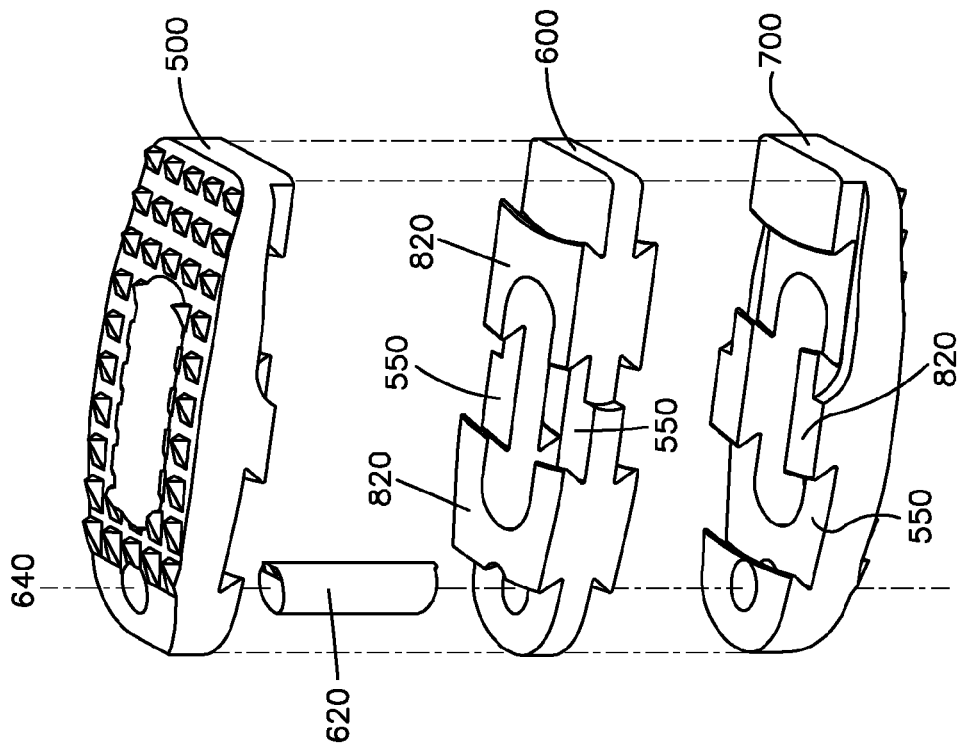
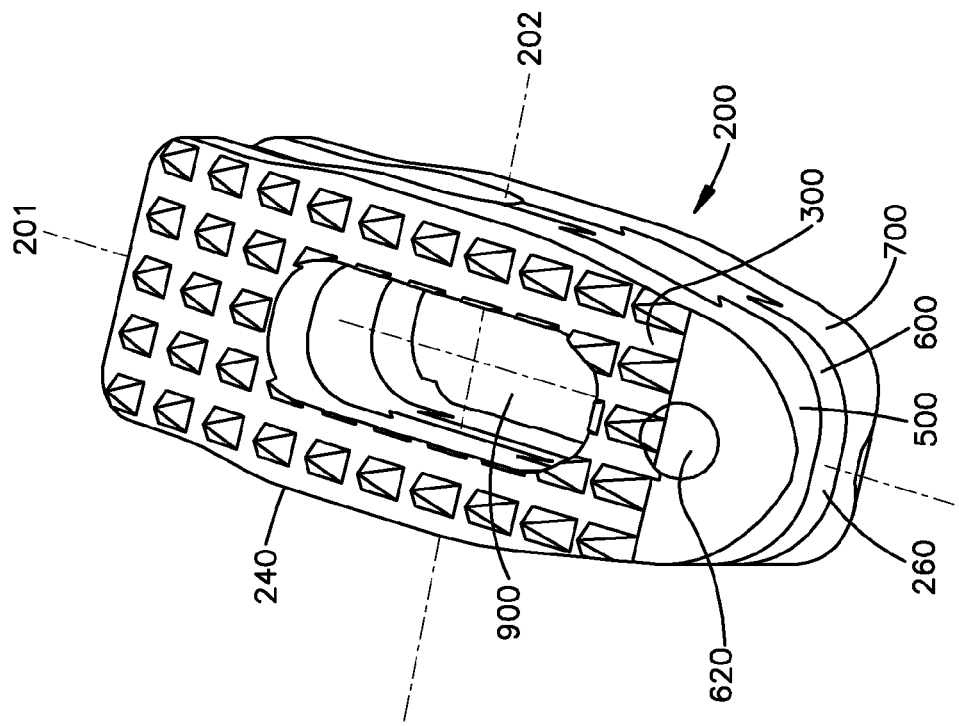
Fig.8C
Fig.8B

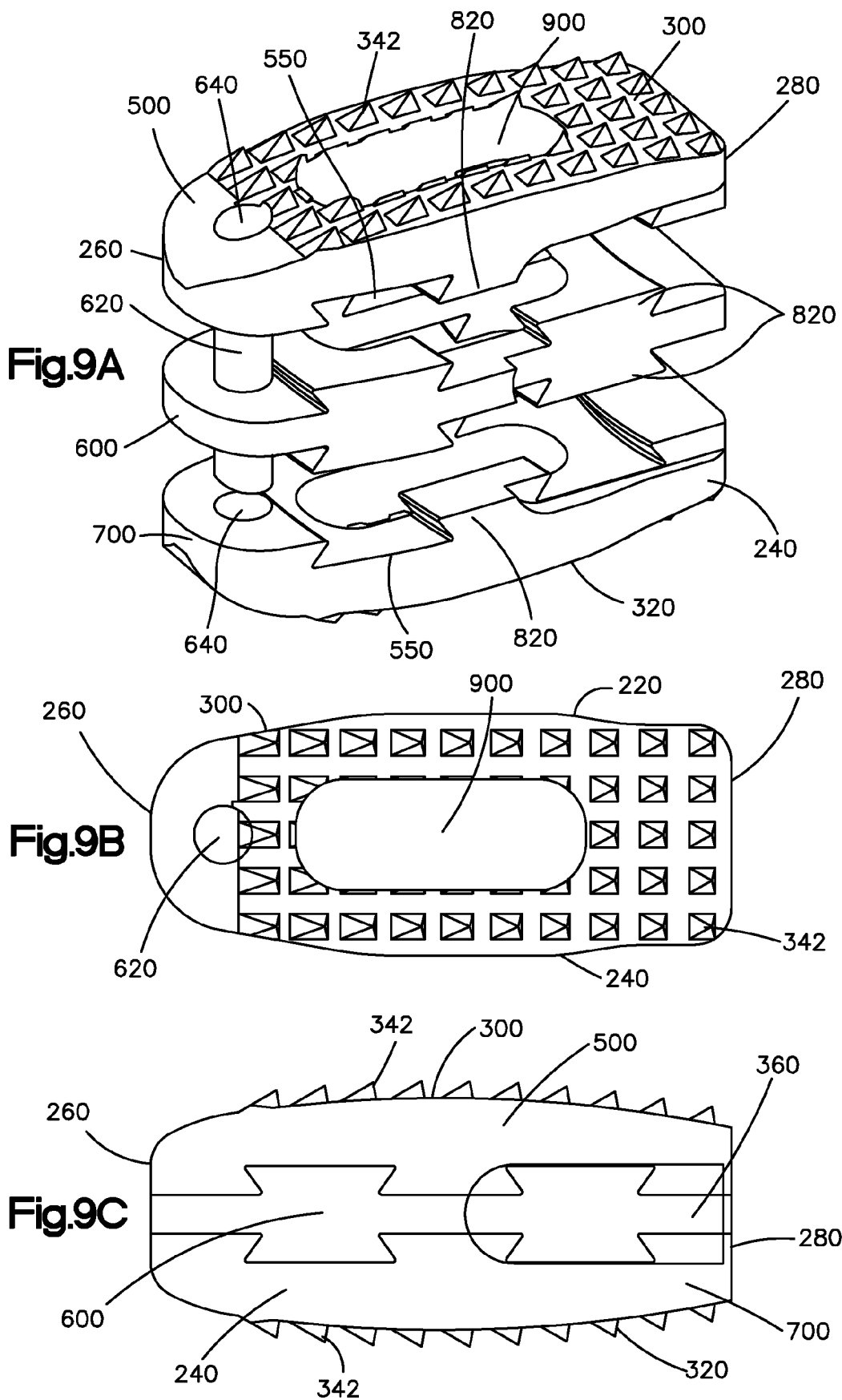

ALLOGRAFT INTERVERTEBRAL IMPLANT AND METHOD OF MANUFACTURING THE SAME

CROSS REFERENCE TO RELATED APPLICATION

This application claims the benefit of U.S. Provisional Application No. 60/844,515 filed Sep. 13, 2006, the entire content of which is expressly incorporated herein by reference thereto.

FIELD OF THE INVENTION

The present invention is directed to an intervertebral implant, more particularly to an intervertebral implant made from two or more pieces of allograft bone.

BACKGROUND OF THE INVENTION

A number of medical conditions such as, for example, compression of spinal cord nerve roots, degenerative disc disease, herniated nucleus pulposus, spinal stenosis and spondylolisthesis can cause severe back pain. Intervertebral fusion is one surgical method for alleviating back pain. In a posterior lumbar interbody fusion ("PLIF") procedure, two adjacent vertebral bodies are fused together by removing the affected intervertebral disc and inserting posteriorly one or more implants on either side of the midline of the spine that would allow for bone to grow between the two adjacent vertebral bodies to bridge the gap left by the removed intervertebral disc.

One variation to the traditional PLIF technique is a transforaminal posterior lumbar interbody fusion ("T-PLIF") procedure. Pursuant to this procedure, an implant is inserted into the affected disc space via a unilateral (or sometimes bilateral), posterior approach, offset from the midline of the spine, by removing portions of the facet joint of the vertebrae. The T-PLIF procedure avoids damage to nerve structures such as the dura, cauda equina and the nerve root, but the resulting transforaminal window available to remove the affected disc, prepare the vertebral endplates, and insert the implant is limited laterally by soft tissue and medially by the cauda equina.

A number of different implants have been specifically developed for use in connection with the PLIF and T-PLIF procedures with varying success. These include titanium or polymer cages and allograft solid bodies. For example, U.S. Pat. No. 6,719,794 to Gerber et al. discloses, inter alia, an intervertebral implant for use in a T-PLIF procedure made from one or more pieces of allograft bone. The multi-piece implant is joined together by a plurality of interlocking surfaces. The implant may further include one or more pins for securing the implant together. However, because of the interlocking surfaces and pins, the intervertebral implant is formed as a solid body implant (e.g., the implant does not contain any through bore for receiving bone graft material). That is, because of the complexities of forming and machining implants from allograft bone as compared to forming and machining implants from a metal, polymer, etc., manufacturers have been unable to manufacture implants sized and configured for PLIF and T-PLIF procedures that include one or more through bores for receiving bone graft material to facilitate bone fusion.

Moreover, known multi-piece allograft implants are generally initially joined together and then the joined pieces are shaped, this may result in less control and in reduced size potential.

There is a need for an improved intervertebral implant made from multiple pieces of allograft bone, wherein the pieces are joined together to enable the implant to remain assembled in situ, structurally support the required spinal loads and preferably to also contain one or more through-bores for receiving bone graft material to facilitate bone fusion of the adjacent vertebrae bodies.

SUMMARY OF THE INVENTION

The present invention is directed to an intervertebral implant sized and configured for insertion between adjacent vertebral bodies in a spinal fusion surgery. The implant is preferably manufactured from two or more pieces of allograft bone joined together by a dovetail joint. The dovetail joint being sized and configured to substantially follow the exterior shape or surface (e.g. perimeter) of the intervertebral implant. The dovetail joint may preferably follow a curved surface or line, for example, the dovetail joint preferably follows the contours of the curved front and back surfaces of the implant. The intervertebral implant may also include one or more bone pins for joining the allograft pieces, the pins being inserted into the implant at an angle substantially vertical and/or perpendicular with respect to the interfacing surface of the dovetail joint. The intervertebral implant may also include one or more central through-bores for receiving ostegenic or bone graft material. The intervertebral implant is preferably sized and configured for insertion in a T-PLIF or PLIF procedure.

In one exemplary embodiment, the intervertebral implant is sized and configured for implantation between first and second adjacent vertebra via a transforaminal lumbar interbody fusion technique. The implant including an allograft body formed from at least two pieces of allograft bone, the body including a curved front surface, a curved back surface, a pair of ends, preferably curved ends, separating the curved front and back surfaces, an upper surface and a lower surface. The upper and lower surfaces preferably being sized and configured for contacting at least a portion of the first and second vertebrae. The curved front and back surfaces preferably defining an outer perimeter of the implant. The at least two pieces of allograft bone are preferably joined together by a dovetail joint, the dovetail joint having a curved shape that substantially follows the contours of the curved front and back surfaces. The dovetail joint may also substantially follow the contours of one of the ends of the implant.

The at least two pieces of allograft bone may each include a hole at least partially formed therein, the hole being sized and configured to receive at least one pin for further securing the pieces of allograft together. The pins being substantially vertical and/or perpendicular with respect to the interfacing surface of the dovetail joint.

The implant further including at least one through-bore extending from the upper surface to the lower surface, the through-bore being sized and configured to receive bone grafting material for facilitating spinal fusion.

In another exemplary embodiment, the intervertebral implant may be sized and configured for implantation between first and second adjacent vertebra via a posterior lumbar interbody fusion procedure. The implant including an allograft body formed from at least two pieces of allograft bone, the body including an anterior surface, a posterior surface, a pair of lateral side surfaces, an upper surface and a lower surface. The upper and lower surfaces being sized and configured for contacting at least a portion of the first and second vertebrae. The at least two pieces of allograft bone preferably being joined together by at least one dovetail joint, the at least one dovetail joint being orientated substantially transverse to a longitudinal axis of the implant.

The at least two pieces of allograft bone may each include a hole at least partially formed therein, the hole being sized and configured to receive at least one pin for further securing the pieces of allograft together. The pins being substantially vertical and/or perpendicular with respect to the interfacing surface of the dovetail joint.

The implant further including at least one through-bore extending from the upper surface to the lower surface, the through-bore being sized and configured to receive bone grafting material for facilitating spinal fusion.

The present invention is further directed to a method for manufacturing an allograft implant from two or more individual pieces. The method preferably including the steps of: (a) obtaining one or more pieces of allograft bone, (b) shaping the individual implant pieces out of allograft bone into their desired shaped, the desired shape including forming one of either the recess or projection portion of a dovetail joint, and (c) joining the individual pieces together by sliding the individual members together via the dovetail joint. Forming the portions of the dovetail joint may include forming one or more of either the recess or projection portion of the dovetail joint in a single piece, the recess or projection portion may be formed in more than one surface. The method may further include removing the individual pieces from the allograft bone.

The method may further include the steps of forming one or more holes preferably through holes into one or more of the individual pieces, the holes being sized and configured to receive bone pins. The method may also include forming one or more through-bores into the implant for receiving bone graft material for facilitating spinal fusion. The step of forming the holes and/or through-bore may occur either before or after the individual pieces have been joined together.

BRIEF DESCRIPTION OF THE DRAWINGS

The system is explained in even greater detail in the following exemplary drawings. The drawings are merely exemplary to illustrate the structure of preferred devices and certain features that may be used singularly or in combination with other features. The invention should not be limited to the embodiments shown.

FIG. 2A is another perspective view of an exemplary embodiment of a T-PLIF implant;

FIG. 2B is a top view of an exemplary embodiment of a T-PLIF implant shown in FIG. 2A;

FIG. 2C is a perspective view depicting the first and second members of the exemplary embodiment of the T-PLIF implant shown in FIG. 2A;

FIG. 2D is another perspective view depicting the first and second members of the exemplary embodiment of the T-PLIF implant shown in FIG. 2A;

FIG. 4A is a perspective view of another exemplary embodiment of a T-PLIF implant;

FIG. 4B is a cross-sectional view of the T-PLIF implant shown in FIG. 4A;

FIG. 5 is a schematic representation of another exemplary embodiment of a T-PLIF implant;

FIG. 6A depicts one or more steps for manufacturing an exemplary embodiment of a T-PLIF implant in accordance with one aspect of the present invention;

FIG. 6B depicts one or more steps for manufacturing an exemplary embodiment of a T-PLIF implant in accordance with one aspect of the present invention;

FIG. 6C depicts one or more steps for manufacturing an exemplary embodiment of a T-PLIF implant in accordance with one aspect of the present invention;

FIG. 6D depicts one or more steps for manufacturing an exemplary embodiment of a T-PLIF implant in accordance with one aspect of the present invention;

FIG. 6E depicts one or more steps for manufacturing an exemplary embodiment of a T-PLIF implant in accordance with one aspect of the present invention;

FIG. 6F depicts one or more steps for manufacturing an exemplary embodiment of a T-PLIF implant in accordance with one aspect of the present invention;

FIG. 8B is another perspective view of the PLIF implant shown in FIG. 7;

FIG. 8C is a perspective view depicting the first and second members of the PLIF implant shown in FIG. 7;

FIG. 9A is a perspective view of an exemplary embodiment of a PLIF implant;

FIG. 9B is a top view of the PLIF implant shown in FIG. 9A; and

FIG. 9C is a side view of the PLIF implant shown in FIG. 9A.

DETAILED DESCRIPTION OF THE PREFERRED EMBODIMENTS

Certain exemplary embodiments of the invention will now be described with reference to the drawings. In general, such embodiments relate to an intervertebral implant for insertion between adjacent vertebral bodies to restore vertebrae spacing wherein the implant is sized and configured for use as an intervertebral spacer in a spinal fusion surgery, wherein an affected disk is removed from between two adjacent vertebrae and replaced with the implant. The implant preferably provides segmental stability and allows for bone to grow in-between the two adjacent vertebrae to bridge the gap created by disk removal. By way of non-limiting example, the intervertebral implant may be made from two or more pieces of allograft bone. The invention may have other applications and uses and should not be limited to the structure or use described and illustrated. As will be described in greater detail below, the intervertebral implant may include two or more pieces of allograft bone joined together by way of, for example, a dovetail joint. Preferably, as will be described in greater detail below, the dovetail joint is sized and configured to substantially follow at least a portion of the exterior shape or surface (e.g. perimeter) of the intervertebral implant. For example, the dovetail joint is preferably sized and configured to substantially follow two or three surfaces of the implant such as, for example, the curved front and back surfaces of the implant or the curved front and back surfaces and one of the end surfaces of the implant. The intervertebral implant may also include one or more bone pins for joining the allograft pieces. The intervertebral implant may also include one or more through-bores for receiving ostegenic or bone graft material. The intervertebral implant is preferably sized and configured for insertion during a T-PLIF procedure. Alternatively, the intervertebral implant may be sized and configured for insertion during a PLIF procedure.

Figure 1A:
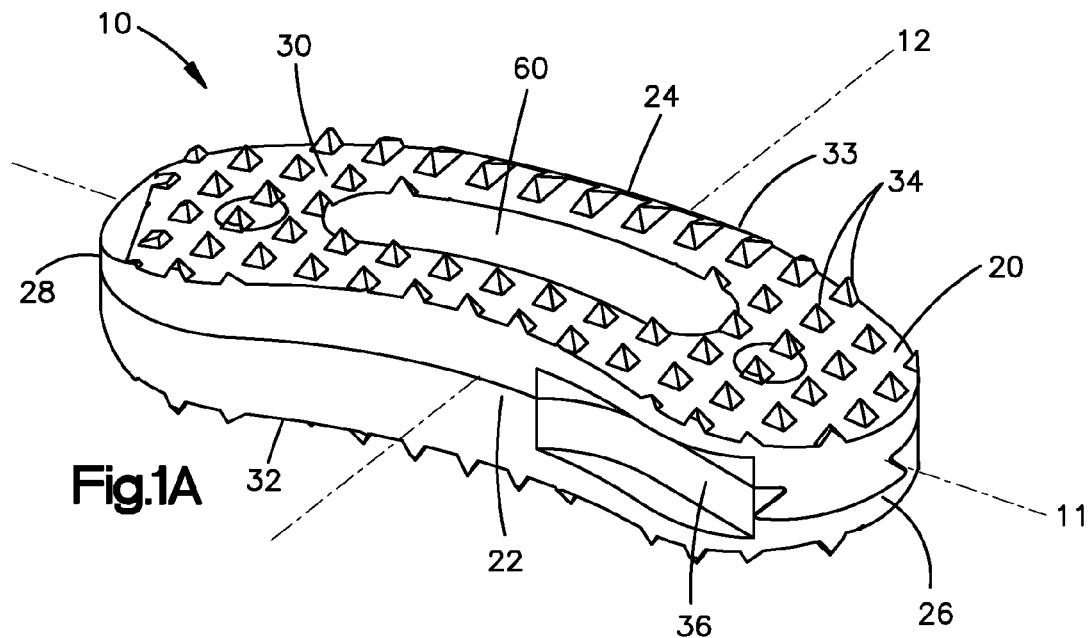
FIG. 1A is a perspective view of an exemplary embodiment of a T-PLIF implant.
Figures 1B, 1C:
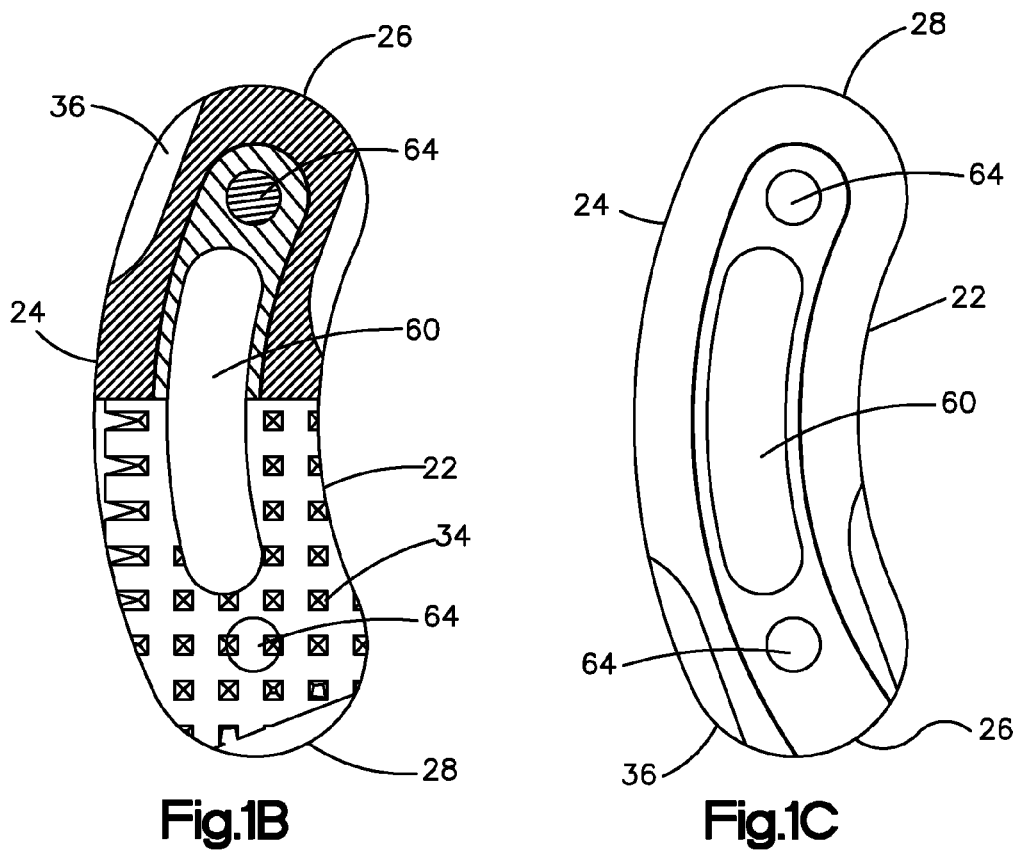
FIG. 1B is a partial top view, partial cross-sectional view of the T-PLIF implant shown in FIG. 1A.
FIG. 1C is a cross-sectional of the T-PLIF implant shown in FIG. 1A.

In FIGS. 1A-1C an exemplary embodiment of a T-PLIF implant 10 is shown. The T-PLIF implant 10 may include a curved body 20. The body 20 may include a curved front surface 22, a curved back surface 24, a pair of narrow ends 26, 28 separating the curved front and back surfaces 22, 24, an upper surface 30 and a lower surface 32. The upper and lower surfaces 30, 32 are preferably sized and configured to contact at least a portion of the endplates of the adjacent vertebral bodies. Alternatively, the T-PLIF implant 10 may take on various other profiles and exterior geometries, depending on the area of the spine to be treated. The curved front and back surfaces 22, 24 facilitate the offset insertion of the T-PLIF implant 10 through the narrow transforaminal window and into the disk space. The narrow ends 26, 28 may be rounded (as shown) or blunt. The upper and lower surfaces 30, 32 may include projections 33, such as, for example, a plurality of teeth 34 for engaging the adjacent vertebrae. The projections 33 formed on the upper and lower surfaces 30, 32 preferably provide a mechanical connection between the T-PLIF implant 10 and the end plates by penetrating at least a portion of the end plates. The initial mechanical stability afforded by incorporation of the projections 33, and in particular the teeth 34, minimizes the risk of post-operative expulsion and/or slippage of the T-PLIF implant 10. It should be noted that the T-PLIF implant 10 may include other forms of projections 33 aside from teeth 34 including, for example, ridges, grooves, threads, etc.

The T-PLIF implant 10 may also include one or more channels 36. Preferably, the channel 36 extends from one of the ends 26, 28 of the T-PLIF implant 10 (shown as end 26). The channel 36 is preferably sized and configured to engage a surgical instrument, such as an implant holder. Preferably, the T-PLIF implant 10 is formed with at least two channels 36, one on each of the front and back surfaces 22, 24. The channels 36 being sized and configured with a curved surface to substantially follow the curved surfaces of the front and back surfaces 22, 24. It should be noted however that the T-PLIF implant 10 may be configured with a single channel 36 formed on only one of the surfaces 22, 24 thereof. Alternatively, the channel 36 may be formed on the upper and/or lower surfaces 30, 32 of the T-PLIF implant 10, or any other surface thereof. Alternatively, the T-PLIF implant 10 may be configured without channels altogether. Other methods for engaging the T-PLIF implant 10 with surgical instruments, such as a threaded hole for receiving the threaded end of a surgical tool or a non-threaded hole for receiving an expandable head of an insertion tool, may also be used.

As shown in FIGS. 2A-2D, the T-PLIF implant 10 may be constructed from two or more pieces. This multi-piece configuration may be particularly useful for implants formed of allograft bone, since it may be difficult and/or impractical to obtain a single, sufficiently large piece of allograft for some applications. The T-PLIF implant 10 may be formed by a first member 50 and a second member 80. Although the T-PLIF implant 10 may be formed from more or less pieces. The first member 50 may be joined to the second member 80 by any means. Preferably, the first member 50 is joined to the second member 80 by a dovetail joint.

Figure 3C:
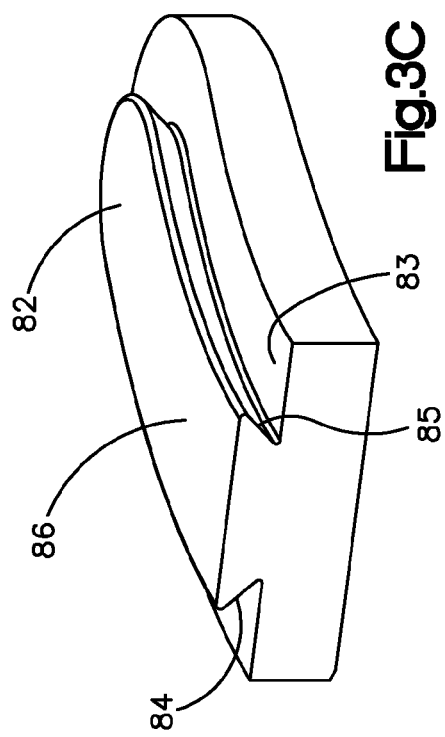
FIG. 3C is another perspective view of the second member shown in FIG. 3A.
Figure 3A:
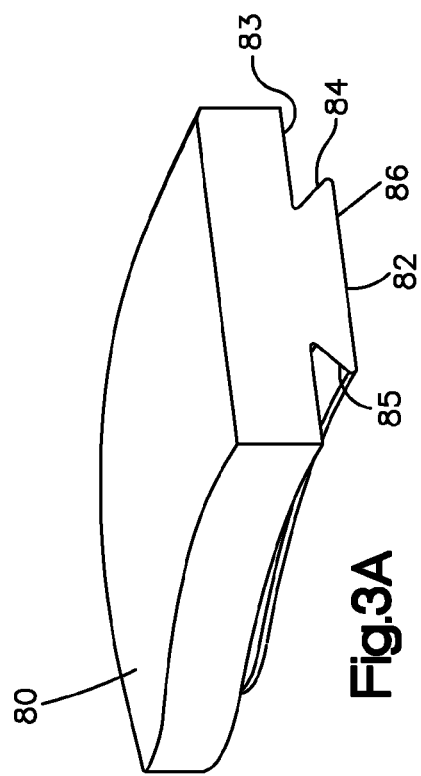
FIG. 3A is a perspective view of an exemplary embodiment of a second member of an exemplary embodiment of a T-PLIF implant.
Figure 3B:
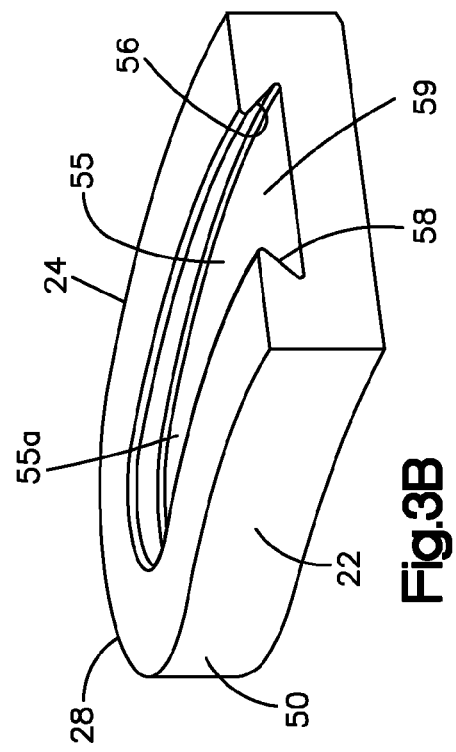
FIG. 3B is a perspective view of an exemplary embodiment of a first member of an exemplary embodiment of a T-PLIF implant.
Figure 6H:
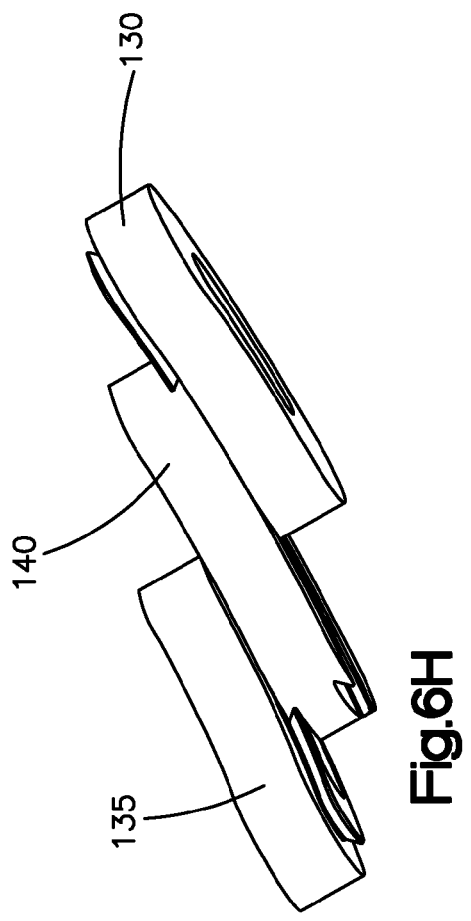
FIG. 6H depicts one or more steps for manufacturing an exemplary embodiment of a T-PLIF implant in accordance with one aspect of the present invention.
Figure 6J:
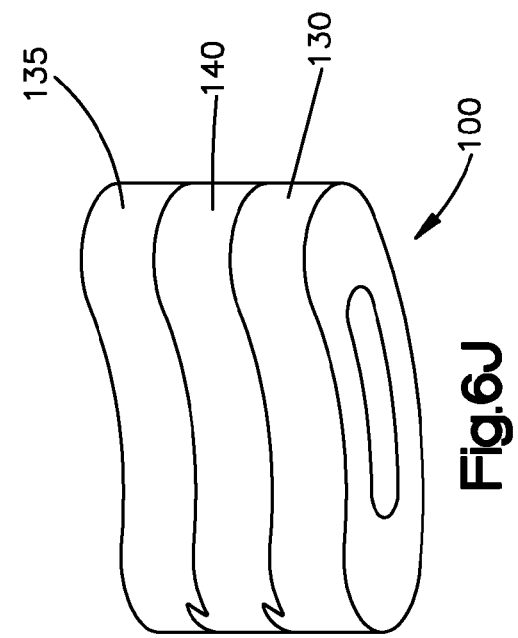
FIG. 6J depicts one or more steps for manufacturing an exemplary embodiment of a T-PLIF implant in accordance with one aspect of the present invention.
Figure 6G:
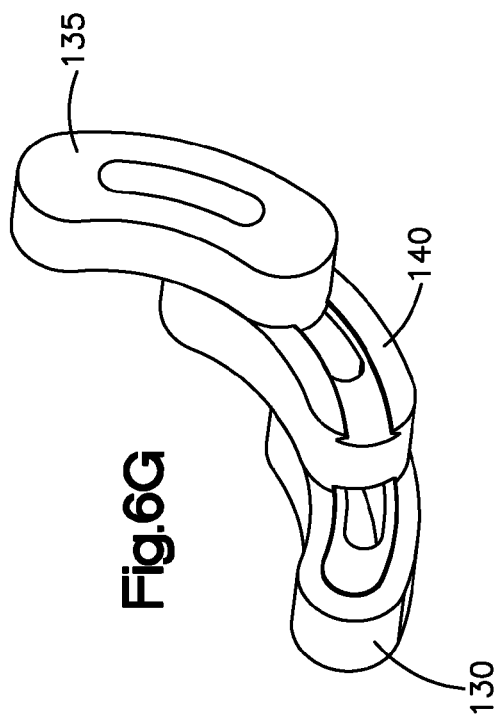
FIG. 6G depicts one or more steps for manufacturing an exemplary embodiment of a T-PLIF implant in accordance with one aspect of the present invention.
Figure 6I:
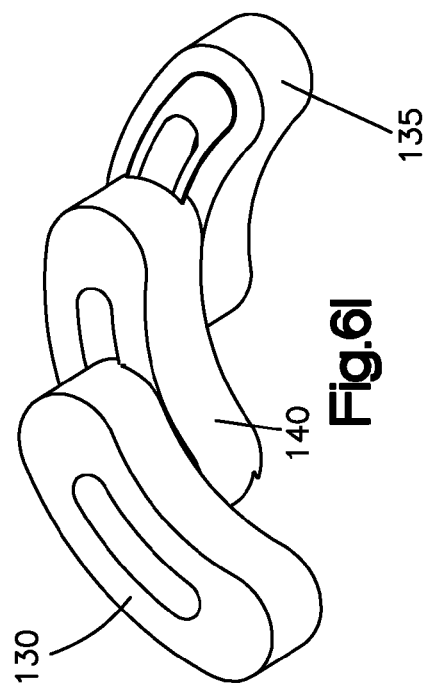
FIG. 6I depicts one or more steps for manufacturing an exemplary embodiment of a T-PLIF implant in accordance with one aspect of the present invention.

As best shown in FIGS. 3A-3C, the first member 50 may include a recess 55 formed therein, the recess 55 being sized and configured to receive a projection 82 formed on and extending from the second member 80. The recess 55 and projection 82 may take on any form. For example, the projection 82 may include a base surface 83, two outwardly tapered side surfaces 84, 85 extending from the base surface 83 and a substantially planar surface 86. As shown, the cross sectional area of the projection 82 may become larger as the distance of the projection 82 from the base surface 83 increases. The recess 55 similarly may include a base surface 55a and two inwardly tapered side surfaces 56, 58 extending from the base surface 55a. As shown, the cross sectional area of the recess 55 may become smaller as the distance of the recess 55 from the base surface 55a increases. The size and configuration of the tapered surfaces 56, 58 formed on the first member 50 being sized and configured to receive the tapered side surfaces 84, 85 of the projection 82 so that, as will be generally appreciated by one of ordinary skill in the art, a dovetail joint is formed. The dovetail joint enables the first and second members 50, 80 to slide with respect to one another, preferably the first and second members 50, 80 slide substantially along the longitudinal axis 11 of the implant 10, while substantially resisting the first and second members 50, 80 from vertically separating.

More preferably, the recess 55 and the projection 82, and hence the dovetail joint, are formed so that they have a curved shape that substantially corresponds with the curved shape of the T-PLIF implant 10. Preferably, the dovetail joint has a curved surface that substantially follows, at least, the contours of the curved front and back surfaces 22, 24. As shown in FIG. 3B, the inwardly tapered surfaces 56, 58 of the recess 55 may be machined in the first member 50 along the front surface 22, the back surface 24, and one of the narrow ends (shown here as 28). The recess 55 may be opened at one of the narrow ends (shown here as 26) thus forming an entry space 59 for slidably receiving the projection 82. In this manner, the recess 55 can slidably receive the projection 82 formed on the second member 80 along the longitudinal axis 11 of the implant 10.

The entry space 59 may be formed with a slightly larger opening to facilitate easier insertion of the projection 82 into the recess 55. The recess 55 may become more narrow towards the rear of the dovetail joint (towards end 28) so that the first and second members 50, 80 can be slid together easily but the dovetail joint becomes tighter as its final position is reached. Alternatively, the recess 55 may have the same dimension throughout. Preferably, the first and second members 50, 80 are sized and configured within sufficient tolerance so that once the projection 82 is fully inserted into the recess 55 the first and second members 50, 80 resist separation of the first and second members 50, 80. That is, the first and second members 50, 80 may be sized and configured so that when the projection 82 is fully inserted into the recess 55, a press-fit type connection is achieved. While it has been described and shown as if the projection 82 is slidably receivable within the recess 55 via one of the narrow ends 26, 28 it should be understood that the projection 82 may be slidably receivable into the recess 55 via one of the front and/or back surfaces 22, 24, or any other surface thereof.

The second member 80 is preferably sized and configured so that once fully inserted into the first member 50, the outer surface of the implant 10 is substantially smooth and devoid of any gap formed by the dovetail joint. For example, the second member 80 may include a ledge 88 (as best shown in FIG. 2D) formed on an end thereof, the ledge 88 being sized and configured to cover the entry space 59 of the recess 55.

The T-PLIF implant 10 may also include one or more pins 62 for securing the first and second members 50, 80, as best shown in FIGS. 2A-2D. The pins 62 may take on any configuration including but not limited to circular, elliptical, oval, square, rectangular, star shaped, etc. The pins 62 may be secured within the implant 10 in a variety of ways, preferably, the T-PLIF implant 10 may include one or more holes 64 for receiving the pins 62. The pins 62 and respective holes 64 may be sized so that they extend from the upper surface 30 to the lower surface 32. Alternatively, the pins 62 and respective holes 64 may be sized so that they extend only through a portion of the height of the implant 10. The pins 62 may be secured within the corresponding holes 64 by any means including but not limited to press-fit, adhesive, mechanical connection such as, for example, threaded connection, etc.

The T-PLIF implant 10 may incorporate substantially straight pins 62. More preferably, by incorporating a joint, such as, for example, a dovetail joint that resists vertical separation of the first and second members with respect to one another, the pins 62 may extend substantially vertical and/or perpendicular with respecting to the interfacing surface of the joint. The pins 62 may intersect the interfacing surface of the joint at an angle $\omega$, preferably at a substantially ninety-degree angle with respect to the interfacing surface of the joint. The incorporation of substantially straight vertical pins 62 facilitates maximum resistance against the first and second members 50, 80 from sliding apart and enables one or more vertical through-bores 60 to be formed in the implant 10, the through-bore 60 being sized and configured to receive bone graft material to facilitate bone fusion of the adjacent vertebrae bodies. Preferably, the implant 10 includes at least two substantially straight vertical pins 62, one on either side of the through-bore 60, adjacent the ends 26, 28 of the implant 10. Preferably, the pins 62 will be as far apart as possible to maximize the size of the vertical through-bore 60. A larger through-bore 60 may allow the surgeon to pack additional bone graft and other bone growth inducing material into the implant 10. It should be understood however that the number, location and/or orientation of the pins 62 can be varied, for example, one, three or more pins 62 may also be used. Additionally, the pins 62 may be placed obliquely or at an angle with respect to the interfacing surface of the joint.

The T-PLIF implant 10 may alternatively include two or more vertical through-bores 60 extending from the upper surface 30 to the lower surface 32 of the implant 10. Alternatively and/or in addition, the T-PLIF implant 10 may include one or more horizontal bores (not shown). The horizontal bores may extend from the back surface 22 to the front surface 24 or from one or both of the ends 26, 28. Alternatively, the implant 10 may not include any bores, vertical or horizontal.

While the T-PLIF implant 10 has been generally described as incorporating a first member 50 and a second member 80, wherein the first and second members 50, 80 are located one on top of the other, it should be understood that, as best shown in FIGS. 4A and 4B, the first and second members 50, 80 may be arranged in a side by side configuration. As shown in this configuration, the T-PLIF implant 10 may include a substantially straight dovetail configuration extending from the upper surface 30 to the lower surface 32. Moreover, as best shown in FIG. 4B the pins 62 may be generally oriented perpendicular to the dovetail joints. Alternatively, the pins 62 may be oriented at an acute angle $\delta$ with respect to the longitudinal axis 11 of the implant 10.

While the T-PLIF implant 10 has been described as being formed from first and second members 50, 80, it should be understood that the T-PLIF implant 10 may include three or more pieces and/or members. As best shown in FIG. 5, for example, the T-PLIF implant 100 may be formed from a first member 130, a second member 135 and a third member 140. As best shown in FIGS. 6G-6J, the first and second members 130, 135 may be formed with projections 82, while the third member 140 may be formed with a pair of recesses 55 for engaging the projections 82 formed on the first and second members 130, 135. Alternatively, the third member 140 may be formed with a pair of projections 82 and the first and second members 130, 135 may be formed with recesses 55 for securing the projections 82. Alternatively, the third member 140 may be formed with both a projection 82 and a recess 55 while one of the first and second members 130, 135 may be formed with a recess 55 for engaging the projection 82 formed on the third member 140. The other of the first and second members 130, 135 being formed with a projection 82 for engaging with the recess 55 formed on the third member 140. The orientation of the members may be provided in any appropriate combination.

The dimensions of the T-PLIF implant 10 can be varied to accommodate a patient's anatomy. For example, the length of the T-PLIF implant 10, as generally measured by the distance between the ends 26, 28 of the implant 10, may range from about 26 mm to about 33 mm. The width of the T-PLIF implant 10, as generally measured by the distance between the front and back surfaces 22, 24, may range from about 9 mm to about 12 mm. Through a combination of implants, it is envisioned that implants having footprints of, for example, 10 mm×27 mm, 10 mm×30 mm, 10 mm×33 mm, 12 mm×27 mm, 12 mm×30 mm, and 12 mm×33 mm may be possible.

The height of the T-PLIF implant 10, as generally measured as the distance between the upper and lower surfaces 30, 32 of the implant 10, is generally chosen based on the size of the disk space to be filled. Preferably, the height of the T-PLIF implant 10 is greatest at the mid-section between the two narrow ends 26, 28 and tapers gradually along the longitudinal axis 11 of the implant 10 so that it is thinnest at the narrow ends 26, 28 of the implant 10. The taper is preferably curved and provides a convex configuration for a better anatomical fit, while also facilitating insertion of the implant 10 into the affected disc space. The T-PLIF implant 10 may have a height at its mid-section of about 7.0 mm to about 17.0 mm. The height at the ends 26, 28 of the T-PLIF implant 10 may range from about 1.5 mm to about 2.0 mm less than the height at the mid-section. Alternatively, the height of the T-PLIF implant 10 may remain substantially constant throughout the implant 10. The height of the T-PLIF implant 10 preferably does not taper or change along the shorter axis 12 (e.g. axis transverse to the longitudinal axis 11) of implant 10. Thus for any given cross section taken perpendicular to the longitudinal axis 11 of the implant 10, the distance between the upper and lower surfaces 30, 32 remains substantially constant. Alternatively, the height of the implant 10 may change or taper along the shorter axis 12 of implant 10.

In one exemplary embodiment, the T-PLIF implant 10 may be about 30 mm in length. The radius of curvature of the front surface 22 may be about 19 mm. The radius of curvature for the back surface 24 may be about 29 mm. The length of the through-bore 60 may be about 15.5 mm. The length between the holes 64 may be about 20 mm. The diameter of the holes 64 may be about 2.4 mm. These dimensions are not to be construed so as to limit the embodiments discussed above but rather to serve as illustrative examples of possible sizes of these various components.

As generally shown and described in U.S. Pat. No. 6,719,794 entitled Intervertebral Implant for Transforaminal Posterior Lumbar Interbody Fusion Procedure; U.S. Pat. No. 6,974,480 entitled Intervertebral Implant for Transforaminal Posterior Lumbar Interbody Fusion Procedure; U.S. Pat. No. 7,223,292 entitled Intervertebral Implant for Transforaminal Posterior Lumbar Interbody Fusion Procedure, U.S. Pat. No. 7,226,483 entitled Method of Performing a Transforaminal Posterior Lumbar Interbody Fusion Procedure, U.S. patent application Ser. No. 10/787,984 entitled Intervertebral Implant for Transforaminal Posterior Lumbar Interbody Fusion Procedure and U.S. patent application Ser. No. 11/745,293 entitled Intervertebral Implant for Transforaminal Posterior Lumbar Interbody Fusion Procedure, the entire contents of which are all expressly incorporated by reference, the T-PLIF implant is preferably sized and configured for insertion in-between adjacent vertebra via a T-PLIF procedure which generally involves a posterior approach, offset from a midline of the spine, to the affected intervertebral disk space.

In one exemplary T-PLIF procedure, a narrow transforaminal window may be produced to permit insertion of the T-PLIF implant. The transforaminal window is generally limited laterally by the patient's dura and the superior exiting nerve root. In use, the T-PLIF procedure enables the T-PLIF implant to be seated in the disc space behind the dura without disturbing the anterior curtain of the disc space. One exemplary surgical technique for the T-PLIF procedure begins with the patient being placed in a prone position on a lumbar frame. Next, radiographic equipment may be used to assist the surgeon in locating the precise intraoperative position for the T-PLIF implant. Next, an incision may be made. Following incision, the facets, lamina and other anatomical landmarks are identified. The affected vertebrae are then preferably distracted using a lamina spreader or a lateral distractor, both of which are commonly known in the art.

Following distraction, the transforaminal window is preferably created by removing the inferior facet of the cranial vertebrae and the superior facet of the caudal vertebrae using, for example, one or more osteotomes. A discectomy may then be performed during which a portion of, substantially all of, and more preferably all, of the disc material from the affected disc space may be removed using a combination of straight and angled curettes. After the discectomy is complete, the superficial layers of the entire cartilaginous endplates may be removed with a combination of straight and angled bone rasps. This is done to expose bleeding bone, but care should be taken to avoid excess removal of subchondral bone, as this may weaken the anterior column. Entire removal of the endplate may result in subsidence and loss of segmental stability.

Next, an appropriately sized trial-fit T-PLIF spacer may be inserted into the intervertebral disc space using gentle impaction, to determine the appropriate height of the T-PLIF implant for the disc space to be filled. Fluoroscopy can assist in confirming the fit of the trial spacer. Upon identifying and removing the best fitting trial spacer, a T-PLIF implant of appropriate size is selected.

At this time, prior to placement of the T-PLIF implant, bone graft material, such as autogenous cancellous bone or a bone substitute, may be placed in the anterior and lateral aspects of the affected disc space. Moreover, since the T-PLIF implant is preferably formed with a through bore, bone graft material may be inserted into the through-bore. Alternatively, the T-PLIF implant may come pre-arrived with bone graft material packed therein.

During insertion, the T-PLIF implant may be held securely using a surgical instrument such as an implant holder, which may engage the channels formed in or other features in the T-PLIF implant. The tips of the implant holder may be curved or angled to mate with the curved implant and to facilitate insertion of the implant into the disc space. The T-PLIF implant may then be introduced into the intervertebral disc space via the transforaminal window.

A guide tool having a curved blade which preferably matches the curvature of the anterior face of T-PLIF implant may be used to properly guide the T-PLIF implant into the affected disc space. Slight impaction may also be necessary. Once the T-PLIF implant is in the desired final position, the implant holder and optional guide tool are removed and additional bone graft material may be inserted in the anterior and lateral aspects of the affected disc space. Preferably, the T-PLIF implant should be recessed from the anterior edge of the vertebral body. Moreover, preferably the curvature of the anterior face of the implant is substantially the same as the curvature of the anterior edge of the disc space.

Figure 7:
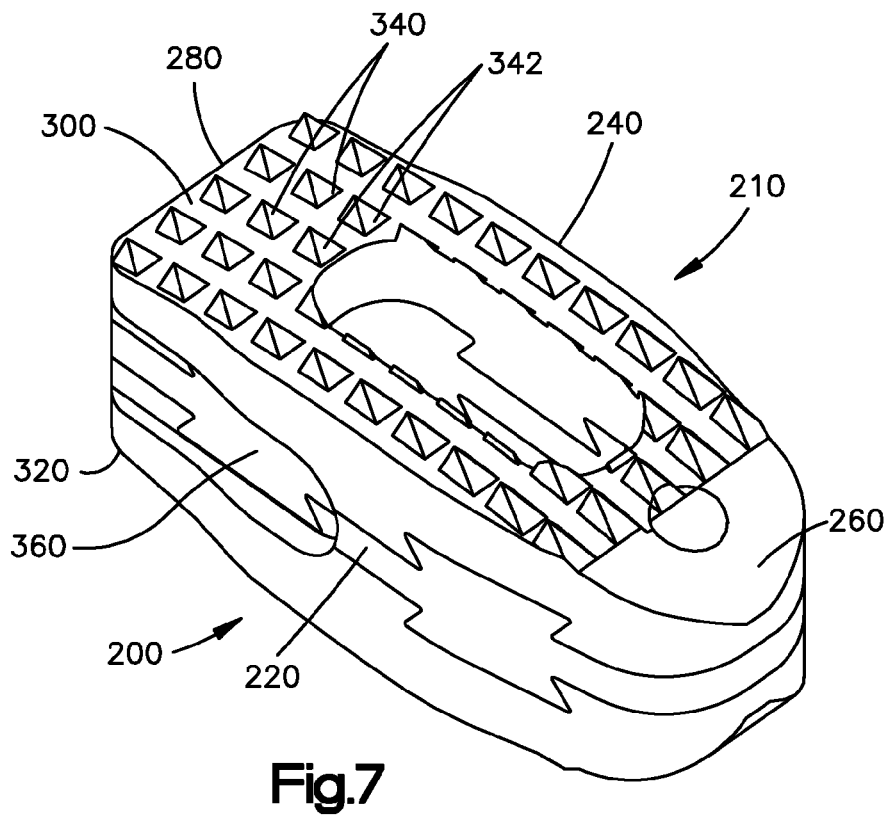
FIG. 7 is a perspective view of an exemplary embodiment of a PLIF implant.
Figure 8A:
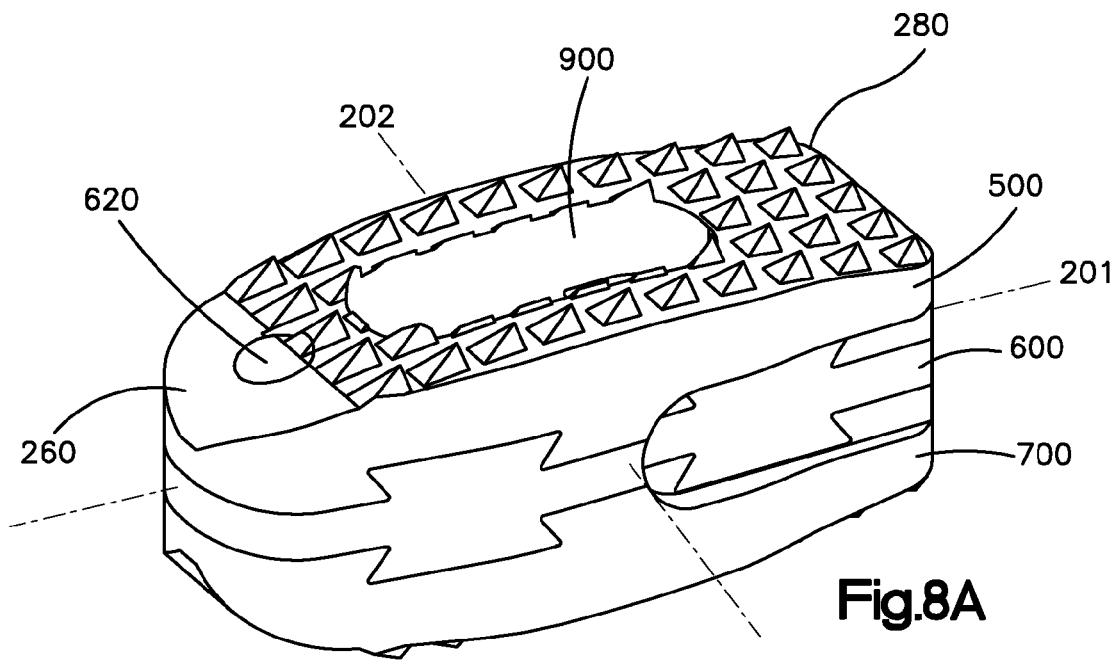
FIG. 8A is another perspective view of the PLIF implant shown in FIG. 7.

Alternatively, the intervertebral implant may be sized and configured for insertion during a PLIF procedure. As best shown in FIG. 7, the PLIF implant 200 may include a body 210, the body 210 may include an anterior surface 260, a posterior surface 280, a pair of lateral side surfaces 220, 240, an upper surface 300 and a lower surface 320. The upper and lower surfaces 300, 320 are preferably sized and configured to contact at least a portion of the endplates of the adjacent vertebral bodies. Alternatively, the PLIF implant 200 may take on various profiles and exterior geometries, depending on the area of the spine to be treated. The upper and lower surfaces 300, 320 may include projections 340, such as, for example, a plurality of teeth 342 for engaging the adjacent vertebrae. The projections 340 formed on the upper and lower surfaces 300, 320 preferably provide a mechanical connection between the PLIF implant 200 and the end plates by penetrating at least a portion of the end plates. The initial mechanical stability afforded by incorporation of the projections 340, and in particular the teeth 342, minimizes the risk of post-operative expulsion and/or slippage of the PLIF implant 200.

The PLIF implant 200 may also include one or more channels 360. Preferably, the channels 360 are formed in one or both of the lateral side surfaces 220, 240 and extend from the posterior surface 280 of the T-PLIF implant 200. The channel 360 is preferably sized and configured to engage a surgical instrument, such as an implant holder. Preferably, the PLIF implant 200 is formed with at least two channels 360, one on each of the lateral side surfaces 220, 240. It should be noted however that the PLIF implant 200 may be configured with a single channel 360 formed on only one surface thereof. Alternatively, the channel 360 may be formed on the upper and/or lower surfaces 300, 320 of the PLIF implant 200, or any other surface thereof. Alternatively, the PLIF implant 200 may be configured without channels altogether. Other methods for engaging the PLIF implant 200 with surgical instruments, such as, for example, a threaded hole for receiving the threaded end of a surgical tool or a non-threaded hole for receiving an expandable head of an insertion tool, may also be used.

The PLIF implant 200 may be constructed from two or more pieces. This multi-piece configuration may be particularly useful for implants formed of allograft bone, since it may be difficult and/or impractical to obtain a single, sufficiently large piece of allograft for some applications. The PLIF implant 200 may be formed by a first member and a second member. The first member may be joined to the second member by any means. Preferably, the first member is joined to the second member by a dovetail joint. Alternatively, the PLIF implant 200 may contain more or less pieces and/or members. For example, as best shown in FIGS. 8A-8C and 9A-9C, the PLIF implant 200 may be formed by a first member 500, a second member 600 and a third member 700. The second member 600 may be joined to the first and third members 500, 700 by any means. Preferably, the second member 600 is joined to the first and third members 500, 700 by dovetail joints.

As shown, the first, second and third members 500, 600, 700 may each include one or more projections 820, one or more recesses 550, and/or one or more projections 820 and recesses 550 for interconnecting with one another. Any combination of recesses 550 and projections 820 may be used. The recess 550 and projection 820 may take on any form. For example, the recess 550 may include two inwardly tapered side surfaces for slidably receiving two outwardly tapered side surfaces formed on the projection 820, as previously described in connection with the T-PLIF implant 10.

As shown, preferably the dovetail joint is sized and configured to permit the first, second and third members 500, 600, 700 to slide with respect to one another substantially along an axis 202 transverse to the longitudinal axis 201 of the implant 200, while substantially resisting the members 500, 600, 700 from vertically separating. Alternatively, the PLIF implant 200 may include a dovetail configuration that substantially follows the contours of the body 210, for example, the contours of the lateral sides surfaces 220, 240, of the PLIF implant 200 as described above in connection with the T-PLIF implant 10.

The PLIF implant 200 may also include one or more pins 620 (similar to pins 62 described above) for further securing the first, second and third members 500, 600, 700 together. The PLIF implant 200 may incorporate substantially straight pins 620. More preferably, by incorporating a joint, such as, for example, a dovetail joint that resists vertical separation of the first, second and third members 500, 600, 700 with respect to one another, the pins 620 may extend substantially vertical and/or perpendicular with respect to the interfacing surface of the joint. The pins 620 may intersect the interfacing surface of the joint at an angle ω, preferably at a substantially ninety-degree angle with respect to the interfacing surface of the joint. The incorporation of substantially straight vertical pins 620 facilitates maximum resistance against the first, second, and third members 500, 600, 700 from sliding apart and enables one or more vertical through-bores 900 to be formed in the implant 200, the bore 900 being sized and configured to receive bone graft material to facilitate bone fusion of the adjacent vertebrae bodies. Preferably, the implant 200 includes at least one substantially straight pin 620. The pin can be located anywhere on the implant 200. Preferably, the pin 620 will be located so as to maximize the size of the vertical through-bore 900. A larger through-bore 900 may allow the surgeon to pack the PLIF implant 200 with more bone graft and other bone growth inducing material. As shown, the pin 620 may be located near the anterior surface 280 of the implant 200. The number, location and/or orientation of the pins 620 can be varied, for example, two or more pins 620 may be used. Additionally, the pins 62 may be placed obliquely or at an angle with respect to the interfacing surface of the joint.

The PLIF implant 200 may alternatively include two or more vertical through-bores 900 extending from the upper surface 300 to the lower surface 320 of the implant 200. Alternatively, and/or in addition, the PLIF implant 200 may include one or more horizontal bores (not shown). The horizontal bores may extend from one or both of the lateral side surfaces 220, 240 or from one or both of the posterior and anterior surfaces 260, 280. Alternatively, the implant 200 may not include any through bores, either vertical or horizontal.

The dimensions of the PLIF implant 200 can be varied to accommodate a patient's anatomy. For example, the length of the PLIF implant 200, as generally measured by the distance from the anterior surface to the posterior surface, may range from about 18 mm to about 32 mm. The width of the PLIF implant 200, as generally measured by the distance between the two lateral side surfaces, may range from about 6 mm to about 14 mm. Through a combination of multiple piece design implants having footprints, for example, 6×18 mm, 14×32 mm, etc. may be possible.

The height of the PLIF implant 200, as generally measured by the distance between the upper and lower surfaces, is generally chosen based on the sized of the disk space to be filled. Preferably, the height of the PLIF implant 200 is greatest at the a point in between the mid-section and the anterior surface 260 and tapers gradually along the longitudinal axis 201 of the implant 200 so that it is thinnest at the posterior surface 260 of the implant 200. The taper is preferably curved and provides a convex configuration for a better anatomical fit, while also facilitating insertion of the implant 200 into the affected disc space. The PLIF implant 200 may have a height at its anterior surface of about 7 mm to about 17 mm and a height at its posterior surface of about 4.6 mm to about 13.7 mm. Alternatively, the height of the PLIF implant 200 may remain substantially constant throughout the implant 200. The height of the PLIF implant 200 preferably does not taper or change along the shorter axis 202 of the PLIF implant 200. Thus for any given cross section taken perpendicular to the longitudinal axis 201 of the PLIF implant 200, the distance between the upper and lower surfaces 300, 320 remains substantially constant. Alternatively, the height of the PLIF implant 200 may change or taper along the shorter axis 202 as well.

As generally shown and described in U.S. Pat. No. 6,986,788 entitled Intervertebral Allograft Spacer; U.S. Pat. No. 6,554,863 entitled Intervertebral Allograft Spacer, U.S. Pat. No. RE 38,614 entitled Intervertebral Allograft Spacer, U.S. patent application Ser. No. 11/150,584 entitled Intervertebral Allograft Spacer and U.S. patent application Ser. No. 11/150,608 entitled Intervertebral Allograft Spacer, the entire contents of which are all expressly incorporated by reference, the PLIF implant is preferably sized and configured for insertion in-between adjacent vertebra via a PLIF procedure which generally involves insertion of two PLIF implants via a posterior approach, on either side of a midline of the spine, to the affected intervertebral disk space.

One exemplary surgical technique for the PLIF procedure begins with the patient being placed in a prone position on a lumbar frame. Next, radiographic equipment may be used to assist the surgeon in locating the precise intraoperative position for the PLIF implant. Next, an incision may be made and the patient's skin may be dissected from the midline laterally. Following incision, the spinous process, lamina, dura, nerve roots, and other anatomical landmarks are identified. The affected vertebrae are then preferably distracted using a lamina spreader or a lateral distractor, both of which are commonly known in the art. The surgeon may then perform a laminotomy to the medial aspect of the facet and reflects dura to expose a small window (e.g. approximately 13 mm) to the disc space. Next a discectomy may be performed during which substantially all of, and more preferably all, of the disc material from the affected disc space may be removed through the window. After the discectomy is complete, the superficial layers of the entire cartilaginous endplates may be removed. This is done to expose bleeding bone, but care should be taken to avoid excess removal of subchondral bone, as this may weaken the anterior column. Entire removal of the endplate may result in subsidence and loss of segmental stability.

Next, an appropriately sized trial-fit PLIF spacer may be inserted into the intervertebral disc space using gentle impaction, to determine the appropriate height of the PLIF implant for the disc space to be filled. Fluoroscopy can assist in confirming the fit of the trial spacer. Upon identifying and removing the best fitting trial spacer, a PLIF implant of appropriate size is selected.

At this time, prior to placement of the PLIF implant, bone graft material, such as autogenous cancellous bone or a bone substitute, may be placed in the anterior and lateral aspects of the affected disc space. Moreover, since the PLIF implant is preferably formed with a through bore, bone graft material may be inserted into the through-bore. Alternatively, the PLIF implant may come pre-arrived with bone graft material packed therein.

During insertion, the PLIF implant may be held securely using a surgical instrument such as an implant holder, which may engage the channels or slots formed on the PLIF implant. The first PLIF implant may then be introduced into the intervertebral disc space.

Regardless of which side of the spinous process the implant is inserted in, autogenous cancellous bone or a bone substitute should be placed in the anterior and medial aspect of the vertebral disc space prior to placement of the second PLIF implant. The distractor may then be removed and a second PLIF implant of the same height as the first PLIF implant may be inserted into the space, using gentle impaction as before. Preferably, the implants are recessed 2-4 mm beyond the posterior rim of the vertebral body.

Alternatively, it should be noted that the T-PLIF and PLIF implants may be inserted using minimally invasive procedures.

Referring back to FIGS. 6A-6J, an exemplary method for manufacturing a multi-piece allograft implant will now be described and shown in connection with the T-PLIF implant. However, it should be understood that the PLIF implant may be similarly manufactured.

The members, such as, for example, the first and second members 50, 80 or the first, second and third members 130, 135, 140, of the implant may be individually formed (e.g. machined, sized, shaped, etc.) before assembling the T-PLIF implant. The individual members may be first roughly shaped on the pre-selected bone 150, which may have been obtained, for example, from a cadaver. The individual members of the implant may be oriented such that the Haversian canals of each bone portion 150 may be substantially aligned to be roughly perpendicular to the upper and lower surfaces of the implant. This orientation of the bone portions 150 may provide an implant having maximum strength in the vertical direction. This orientation of the bone portions 150 may also provide the benefit of readily allowing blood and/or osteogenic materials to flow through the canals between the vertebral end plates, thus facilitating fusion of the implant with the adjacent vertebrae.

After forming the individual members into their desired shapes, the desired shape including forming one of either the recess or projection portion of a dovetail joint, the individual members may be removed and/or dislodged from the pre-selected bone 150. Next, the individual members may be assembled by sliding together, via the dovetail joint, to create the implant as shown in FIGS. 6D-J.

Next, one or more holes may be formed in the implant. The holes being sized and configured to receive one or more pins. Alternatively, the holes may be formed before the individual members have been assembled into the implant.

Alternatively and/or in addition, one or more through bores may be formed in the implant. The through bores being sized and configured to receive bone graft material for facilitating spinal fusion. Alternatively, the bores may be formed before the individual members have been assembled into the implant.

Moreover, after assembling, the projections and/or teeth may be formed into the upper and lower surfaces of the implant. Alternatively, the teeth may be formed into the upper and lower surfaces of the implant before assembly. Additionally, one or more channels may be formed for receiving the implant holder. This step may also occur before or after assembling the implant.

By forming the individual members of the implant before assembling the implant, in particular by shaping the outer shape or surface (e.g. perimeter) of the implant into the base tissue and then joining the members of the intervertebral implant, the following advantages may be achieved. First, individually forming the individual members may allow for a larger material footprint. This may be especially important when forming implants from allograft bone due to limitations of material thicknesses in available base allograft tissue. Second, the individual machining of the dovetail geometry permits one to better control the required complex tool path. For example, by individually forming the members the user has better control over forming and/or shaping the outer shape or surface (e.g. perimeter) of the implant and the curved dovetail joint. Thus, individually forming the members prior to assembly may result in greater size potential of the graft and better control over forming the complex, geometries of the implant and dovetail feature.

As will be appreciated by those skilled in the art, any or all of the components described herein such as, for example, individual members, pins, etc. may be provided in sets or kits so that the surgeon may select various combinations of components to perform a fixation procedure which is configured specifically for the particular needs/anatomy of a patient. It should be noted that one or more of each component may be provided in a kit or set. In some kits or sets, the same component may be provided in different shapes and/or sizes.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. An allograft intervertebral implant sized and configured for implantation between first and second adjacent vertebra via a transforaminal lumbar interbody fusion technique, the implant comprising:
    an allograft body formed from at least two pieces of allograft bone, the body including a curved front surface, a curved back surface, a pair of ends separating the curved front and back surfaces, an upper surface and a lower surface wherein the upper and lower surfaces are sized and configured for contacting at least a portion of the first and second vertebrae, the curved front and back surfaces defining an outer perimeter of the implant, at least one vertical through-bore extending from the upper surface to the lower surface, the vertical through-bore being about half the length of the curved front surface or longer and configured to receive bone graft material;
    wherein the first allograft bone piece has the upper surface and an opposite interface surface, the interface surface configured so that its thickness at the pair of ends is relatively equal, the interface surface containing the first portion of a dovetail joint and the second allograft bone piece has the lower surface and an opposite interface surface, the interface surface configured so that its thickness at the pair of ends is relatively equal, the interface surface containing the second portion of the dovetail joint, the at least two pieces of allograft bone are joined together by the dovetail joint, the dovetail joint having a curved shape that substantially follows the contours of the curved front and back surfaces of the body.

2. The allograft implant of claim 1, wherein the at least two pieces of allograft bone each include at least one hole at least partially formed therein, the hole being sized and configured to receive at least one pin for further securing the pieces of allograft together.

3. The allograft implant of claim 2, wherein each of the ends contains at least one hole formed therein for receiving one of the pins.

4. The allograft implant of claim 2, wherein each of the holes is substantially perpendicular with respect to the dovetail joint.

5. The allograft implant of claim 4, wherein the implant further comprises at least one pin inserted within the hole.

6. The allograft implant of claim 1, further comprising at least one non-threaded, horizontal channel configured and adapted for engagement by an implant insertion tool, the channel being disposed along at least a portion of one of the curved front or back surfaces.

7. The allograft implant of claim 1, wherein the upper and lower surfaces include a plurality of teeth formed thereon.

8. The allograft implant of claim 7, wherein the plurality of teeth are substantially pyramid shaped.

9. The allograft implant of claim 1, wherein at least one end of the upper or lower surfaces includes a rounded or tapered edge.

10. An allograft intervertebral implant sized and configured for implantation between first and second adjacent vertebra via a transforaminallurnbar interbody fusion technique, the implant comprising:
    an allograft body fonned from at least two pieces of allograft bone, the body including a curved front surface, a curved back surface, a pair of ends separating the curved front and back surfaces, an upper surface and a lower surface wherein the upper and lower surfaces are sized and configured for contacting at least a portion of the first and second vertebrae, the curved front and back surfaces defining an outer perimeter of the implant, at least one vertical through-bore extending from the upper surface to the lower surface, the vertical through-bore being sized and configured to receive bone graft material, and at least one substantially vertical hole at least partially formed in each of the at least two pieces of allograft bone, the hole being sized and configured to receive at least one pin for further securing the pieces of allograft bone together;
    wherein the first allograft bone piece has the upper surface and an opposite interface surface, the interface surface configured to be substantially horizontal so that its thickness at the pair of ends is relatively equal, the interface surface containing the first portion of a dovetail joint and the second allograft bone piece has the lower surface and an opposite interface surface, the interface surface configured to be substantially horizontal so that its thickness at the pair of ends is relatively equal, the interface surface containing the second portion of the dovetail joint, the at least two pieces of allograft bone are joined together by the dovetail joint, the dovetail joint having a curved shape that substantially follows the contours of the curved front and back surfaces of the body.

11. The allograft implant of claim 10, wherein the upper and lower surfaces include a plurality of teeth formed thereon.

12. The allograft implant of claim 11, wherein the plurality of teeth are substantially pyramid shaped.

13. The allograft implant of claim 10, further comprising at least one non-threaded, horizontal channel configured and adapted for engagement by an implant insertion tool, the channel being disposed along at least a portion of one of the curved front or back surfaces.

14. The allograft implant of claim 10, wherein each of the holes is substantially perpendicular with respect to the dovetail joint.

15. The allograft implant of claim 10, wherein at least one end of the upper or lower surfaces includes a rounded or tapered edge.

16. The allograft implant of claim 10, wherein the implant further comprises at least one pin inserted within the hole.

17. The allograft implant of claim 10, wherein the vertical through bore is about half the length of the curved front surface or longer.

18. An allograft intervertebral implant sized and configured for implantation between first and second adjacent vertebra via a posterior lumbar interbody fusion procedure, the implant comprising:
    an allograft body formed from at least two pieces of allograft bone, the body including an anterior surface, a posterior surface, a pair of lateral side surfaces, an upper surface and a lower surface wherein the upper and lower surfaces are sized and configured for contacting at least a portion of the first and second vertebrae, the length of the lateral side surfaces extending along a longitudinal axis of the implant body and being at least one and a half times larger than either the anterior or posterior surfaces;
    wherein the first allograft bone piece has the upper surface and an opposite interface surface, the interface surface containing the first portion of at least one dovetail joint, and the second allograft bone piece has the lower surface and an opposite interface surface, the interface surface containing the second portion of the at least one dovetail joint, the at least two pieces of allograft bone are joined together by at least one dovetail joint, each of the at least one dovetail joint extending from the first lateral side surface to the second lateral side surface and being oriented substantially transverse to the a longitudinal axis of the body; and wherein the allograft body further includes at least one vertical through-hole extending from the upper surface to the lower surface and transverse to both the at least one dovetail joint and the longitudinal axis.

19. The allograft implant of 18, wherein the vertical through-bore is about half the length of the lateral side surfaces or longer and configured to receive bone graft material.

20. The allograft implant of 19, wherein the pieces of allograft bone each include at least one hole at least partially formed therein, the hole being sized and configured to receive at least one pin for further securing the pieces of allograft together.

21. The implant of claim 20, wherein the at least one pin is substantially vertical with respect to the dovetail joint.

22. The allograft implant of claim 18, further comprising at least one non-threaded, horizontal channel configured and adapted for engagement by an implant insertion tool, the channel being disposed along at least a portion of one of the curved front or back surfaces.

23. The allograft implant of claim 18, wherein the upper and lower surfaces include a plurality of teeth formed thereon.

24. The allograft implant of claim 23, wherein the plurality of teeth are substantially pyramid shaped.

25. The allograft implant of claim 18, wherein at least one end of the upper or lower surfaces includes a rounded or tapered edge.

26. The allograft implant of claim 18, wherein the implant further comprises at least one pin substantially proximal to at least one end of the upper surface or lower surface.

27. An allograft intervertebral implant sized and configured for implantation between first and second adjacent vertebra via a posterior lumbar interbody fusion technique, the implant comprising:

an allograft body formed from multiple pieces of allograft bone, the body including an anterior surface, a posterior surface, a pair of lateral ends separating the anterior and posterior surfaces, an upper surface and a lower surface wherein the upper and lower surfaces are sized and configured for contacting at least a portion of the first and second vertebrae, at least one vertical through-bore extending from the upper surface to the lower surface, the vertical through-bore being about half the length of the anterior surface or longer, the length of the lateral side surfaces being at least one and a half times larger than either of the anterior or posterior surfaces;

wherein a first allograft bone piece has the upper surface and an opposite interface surface, the interface surface containing the first portion of a first dovetail joint, wherein a second allograft bone piece has the lower surface and an opposite interface surface, the interface surface containing the first portion of a second dovetail joint, wherein a third allograft bone piece has an upper interface surface and a lower interface surface, the upper interface surface containing the second portion of the first dovetail joint, the lower interface surface containing the second portion of the second dovetail joint, and wherein the at least three pieces of allograft bone are joined together by the first dovetail joint and second dovetail joint, each of the first and second dovetail joints extending from the first lateral side surface to the second lateral side surface.

28. The allograft implant of claim 27, having at least one substantially vertical hole at least partially formed in each of the at least three pieces of allograft bone.

29. The allograft implant of claim 28, wherein the hole is sized and configured to receive at least one pin for further securing the pieces of allograft bone together.

30. The allograft implant of claim 27, wherein the vertical through-bore is about half the length of the lateral side surface or longer.

31. The allograft implant of claim 27, wherein the interface surface of the first allograft bone piece has two portions of two dovetail joints extending from a first lateral side to a second lateral side, and the interface surface of the second allograft bone piece has two portions of two dovetail joints extending from a first lateral side to a second lateral side, the two dovetail joints joining the first and second allograft pieces to the third allograft bone piece.

32. The allograft implant of claim 27, wherein the third allograft bone piece has at least four dovetail protrusions, and the first allograft bone piece and second allograft bone piece each have at least two recessed dovetail portions for mating communication with the third allograft bone piece.

33. The allograft implant of claim 27, wherein the first allograft bone piece, the second allograft bone piece, and the third allograft bone piece further each comprise a recess portion, the recess portions together forming a side channel for engaging with an implantation instrument.

* * * * *